United States Patent [19]
White

[11] Patent Number: 5,722,832
[45] Date of Patent: Mar. 3, 1998

[54] METHOD AND MATERIAL FOR TAKING DENTAL IMPRESSIONS

[76] Inventor: Dennis J. White, 51 Nostrand Rd., Cranbury, N.J. 08512

[21] Appl. No.: 764,707

[22] Filed: Dec. 2, 1996

[51] Int. Cl.[6] .................................................. A61C 9/00
[52] U.S. Cl. ............................ 433/214; 433/37; 433/48
[58] Field of Search ............................. 433/214, 48, 37

[56] References Cited

U.S. PATENT DOCUMENTS

| 4,740,159 | 4/1988 | Hamilton et al. | 433/37 |
| 4,923,905 | 5/1990 | Masuhara et al. | 522/24 |
| 4,978,298 | 12/1990 | Eliasz | 433/214 |
| 5,497,913 | 3/1996 | Baker | 222/102 |

*Primary Examiner*—John J. Wilson

[57] ABSTRACT

A dental impression technique is disclosed which actually includes the presents of air pockets within the dental impression material. The technique describes including small sponges into the tray impression material while mixing base and catalyst. Air pockets are thus created evenly within the impression material. Air pockets may also exist by mixing air into material, small premanufactured spheres, or by chemical reaction.

6 Claims, 1 Drawing Sheet

METHOD AND MATERIAL FOR TAKING DENTAL IMPRESSIONS

FIELD OF INVENTION

This invention relates to taking accurate dental impressions, from which indirect dental prosthesis are fabricated.

DESCRIPTION OF PRIOR ART

Heretofore, dental impressions are taken with various forms of dental trays filled with moldable material. The trays used are either pre-made stock trays or custom trays, individually made from a study model.

These impression techniques yield castings or restorations that usually require adjustments, done by the dentist, at time of cementation. The inaccuracies are due to the distortion inherent of the present day impression techniques.

Distortion of dental impressions are caused by forces exerted on the impression material at the time the tray is lifted from the teeth. Forces are created due to vacuum formed over teeth upon tray removal. Further deformation also occurs as impression material stretches to accommodate undercuts of adjacent teeth.

In the recent disclosure by White, application Ser. No. 08/396,478, more accurate castings are now possible with use of a vented tray. This method and apparatus eliminates vacuum over teeth upon tray removal. In application Ser. No. 08/722,854, White further discloses a type of dental shroud to eliminate any undercuts of adjacent teeth. By eliminating undercuts, stretching of impression materials over teeth upon tray removal is minimized.

Although restorations need less adjustment, and the process is more tolerable, further refinement is needed.

Present day techniques do not address the matter of undercuts of the adjacent teeth and oral structures. Impression materials are not resilient enough to compensate for the irregular patterns of the mouth.

OBJECTS AND ADVANTAGES

"One of the most frustrating aspects of dentistry is the restoration that does not fit its preparation. The problem remains despite the introduction of impression materials, such as the polyvinylsiloxane, with low polymerization contraction and excellent stability." R. W. Wassel, et al., J Prosthetic Dent 1991; 65:748–757.

Currently used impression trays inflict trauma to impression material during removal from the mouth. This trauma stresses and distorts impression materials beyond its elastic memory limits, eventually engendering a casting which is inaccurate.

Diagnosis of origin of inaccuracy of castings is difficult due to the complex series of steps involved. Distortion can occur in many areas of the fabrication process. "Making a casting involves a series of controlled compensations for the dimensional changes occurring throughout the process. Because there is always a discrepancy between the tooth and the cast restoration its fit . . . has become an intense preoccupation." Hunter, et. al. J Prosthetic Dent 1990; 64:636–641.

Diagnosis is further limited because of randomness of final fit. Many restorations do fit well and is supportive of present day techniques. Yet, many have an unexplainable poor fit. Dentists and manufacturers have not isolated the damaging effect of impression tray removal.

Undercuts cause an associated compression of the impression material when the tray is lifted. White discloses a type of dental impression shroud. The purpose of the shroud is to minimize the amount of stress on the impression material; which occurs during tray removal. The shroud works by masking the undercuts of the oral structures.

Accurate impressions are now possible for the first time. The inventions of White demonstrate for the first time the fragility of impression materials. The limitations of the materials are now recognized. The shortcomings of the present day materials may be compensated for and still give accurate impressions.

This invention seeks an adjunct to the dental shroud.

The object of this invention is to actually incorporate air pockets within the impression. Air pockets are needed in the impression to allow for safe and controlled internal compression of the dental impression.

With White's demonstration of impression material fragility, it may now seem a logical sequence to incorporate bubbles or air pockets. Heretofore, the addition of bubbles would have minimal effect. Problems were still present regarding vacuum and undercuts. With the elimination of vacuum and masking of undercuts, the benefit of adding bubbles is apparent. The discovery of the fragility of impression material leads way of thinking toward an internal, self compensating system.

The addition of bubbles allows for an internal type of movement of the impression material. It allows for a compensation heretofore not available. The compensation makes a much more forgiving material.

By use of a vented dental impression tray, dental impression shroud, and by the incorporation of air pockets, exact dental impressions are now possible.

Before the discovery of a vented tray used in conjunction with a dental impression shroud the utilization of air pockets is not self evident. Without these aides, occasional porosities in the impression would not lend itself to necessarily better impressions. Researchers would not intuitively know that air bubbles would create a better impression. Conversely, present day techniques discourage inclusion of air pockets. Bubbles are believed to cause distortion. Mixing techniques have evolved that make a uniform mix, free of bubbles. These mixing techniques are demonstrated by all of the manufacturers.

The reader will see that the use of the present disclosure will aid dentists and laboratory technicians in the process of fabricating restorations. Fit is predictable, leaving dentist with a more controllable means to fabricate a quality casting.

The object of this invention is to produce a clinically acceptable restoration from the laboratory with a minimum to no adjustment.

DETAILED DESCRIPTION OF THE INVENTION

Figure 1:
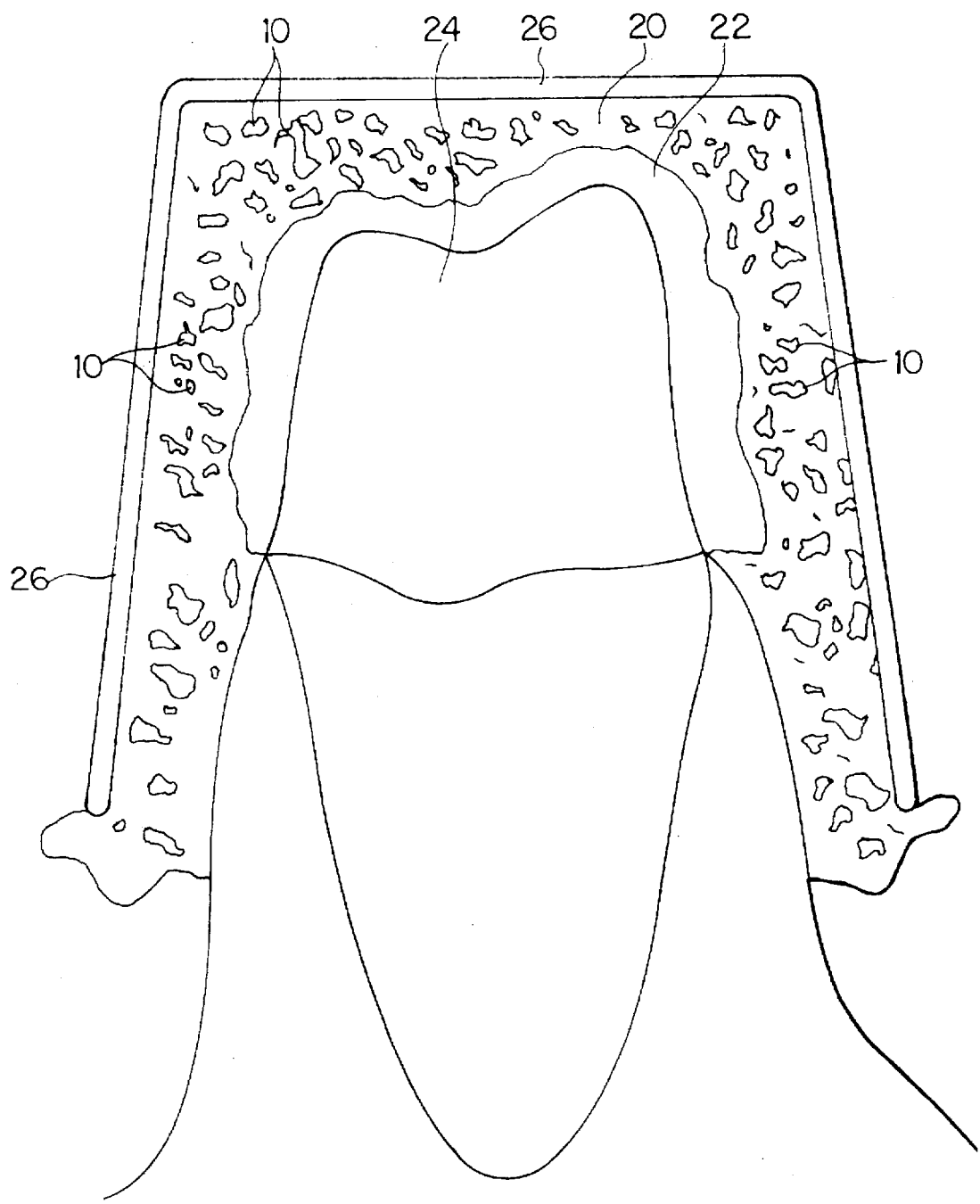
FIG. 1 is a cross sectional view of the present invention.

Tooth preparation is carried out in the normal manner.

The air pockets will be placed away from the actual preparation surface, as to not cause imperfections in desired areas. This may be done by stratifying the impression materials by first syringing impression material against the preparation. Porosity free impression material will be placed against the tooth and the desired air pockets will be in the tray impression material.

When mixing the tray impression material small bubbles are incorporated within the impression material.

Bubbles can be incorporated by addition of small pieces of sponge.

Use of a syringe will place a layer of bubble free impression material, 22, next to the tooth, 24. Then the loaded tray, 26, with impression material, 20, containing bubbles, 10 is placed over the syringe material, 22. Thereby a stratified layering of bubbles is made within the impression, as in FIG. 1.

The core of material, 22, is bubble free and yet the bubbles, 10, will exist within the tray impression material, 20.

Ordinary synthetic sponge can be utilized. Air pockets are easily created because the impression material is too heavy to be appreciably absorbed. Thus, the inner parts of the sponge are a void, leaving the desirable air pockets.

A sponge works well, because in is also conformable. This allows for adaptation within the seated impression tray. The resiliency of the sponge is weak and will not overcome the set impression material. Thus, if the sponge attempts to return to its original shape it will not distort the dental impression.

The size of the sponge can be 3×3×3 mm., or any other size the practitioner may feel appropriate for the size to the tray.

Alternatively, the expanded portion of Super Floss, made by Oral B, could be imbedded into the material around the preparation. The impression material would not be completely absorbed into the expanded floss, and air pockets would exist around the selected tooth.

Prefabricated air pockets could also be utilized. This is in use today as protective shipping material and is called bubble wrap. Air pockets exist in the material used in bubble wrap. A similar material could be applied to dental impressions, imbedding the wrap into the soft impression material before it sets.

Also, prefabricated spheres could be made and included into the impression at time of mixing. This technique would assure a more definitive area of air space within the impression, compared to the inclusion of sponges. Spheres could be made from the actual impression material itself or, vinyl, gelatin capsules, or other material suitable and compatible for the impression material in use.

Similarly, bubbles could be introduced by chemical ingredients. A controlled gas release given off before the set of the impression would make bubbles throughout the tray impression material.

New self mixing units are coming to market, as with the ESPE, Pentamix. Air could be directly injected into the mixing material or spatulating techniques could fold air into the material as it is blended.

CONCLUSIONS, RAMIFICATIONS AND SCOPE OF INVENTION

Thus the reader can see that the dental impression technique disclosed herein is versatile and can be used for onlays, crowns, and bridges. It can be used in any area of the mouth.

Due to superior fit of final restorations, this impression technique has the added benefits in that:

castings have a more predictable fit dentists take less time to seat restoration teeth will have less post-operative sensitivity because of even fitting of crown.

there is greater longevity of the restoration.

Although the description above contains many specifications, these should not be construed as limiting the scope of the invention but as merely providing illustrations of the preferred embodiments of the invention. For example, the impression technique could include any number of ways to include air pockets. Small latex baloons could be used. This disclosure reveals a new concept in dental impression material handling and practioners must use appropriate means to include air pockets within the dental impressions. The demands of specific applications will dictate the avenue by which the bubbles will be incorporated.

Thus the scope of the invention should be determined by the appended claims and their legal equivalents, rather than by the examples given.

I claim:

1. A method of forming dental impression material comprising the steps of, mixing base ingredients needed to form the impression material, and adding a substance that will create air pockets within the impression material when in use.

2. A method as claimed in claim 1 and further including;
the added substance is sponge.

3. A method as claimed in claim 1 and further including;
the added substance is expanded dental floss.

4. A method as claimed in claim 1 and further including;
the added substance has the shape of spheres.

5. A method of taking an impression of teeth comprising the steps of;

preparing a tooth for an impression, syringing substantially porosity free impression material against the tooth, placing impression material containing air pockets in a dental impression tray, and placing the tray with the porous impression material over the tooth and the porosity free impression material, whereby, an impression of the tooth is made that has substantially porosity free impression material in the area next to the tooth, where it is desirable to obtain as smooth an impression as possible, and has an outer layer of impression material containing a significant amount of air pockets, so as to allow the impression material to flex without distorting during use.

6. A dental impression material comprising;

a layer of substantially porosity free material which will contact the dental surface that an impression is being taken of in use, and a layer of material having a significant amount of air pockets formed over said substantially porosity free material, whereby, an impression of the tooth is made, it will have substantially porosity free impression material in the area next to the tooth, where it is desirable to obtain as smooth an impression as possible, and an outer layer of impression material containing a significant amount of air pockets, so as to allow the impression material to flex without distorting during use.

* * * * *